US012724023B2

(12) United States Patent
Busam et al.

(10) Patent No.: US 12,724,023 B2
(45) Date of Patent: Sep. 1, 2026

(54) METHODS AND COMPOSITIONS FOR ASSEMBLY OF BIOLOGICAL NANOPORES

(71) Applicant: Roche Sequencing Solutions, Inc., Pleasanton, CA (US)

(72) Inventors: Robert Busam, Seattle, WA (US); Cynthia Cech, Newcastle, WA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 1162 days.

(21) Appl. No.: 17/661,123

(22) Filed: Apr. 28, 2022

(65) Prior Publication Data

US 2022/0252572 A1 Aug. 11, 2022

Related U.S. Application Data

(63) Continuation of application No. PCT/US2020/057970, filed on Oct. 29, 2020.

(60) Provisional application No. 62/928,207, filed on Oct. 30, 2019.

(51) Int. Cl.

| | |
|---|---|
| ***G01N 33/487*** | (2006.01) |
| ***B82Y 40/00*** | (2011.01) |
| ***C12Q 1/6869*** | (2018.01) |

(52) U.S. Cl.

CPC ........ *G01N 33/48721* (2013.01); *B82Y 40/00* (2013.01); *C12Q 1/6869* (2013.01); *C12Q 2525/131* (2013.01); *C12Q 2525/197* (2013.01); *C12Q 2565/631* (2013.01)

(58) Field of Classification Search

None

See application file for complete search history.

(56) References Cited

U.S. PATENT DOCUMENTS

| | | | |
|---|---|---|---|
| 7,083,958 | B2 | 8/2006 | Sligar et al. |
| 7,662,410 | B2 | 2/2010 | Sligar et al. |
| 7,691,414 | B2 | 4/2010 | Sligar et al. |
| 7,939,259 | B2 | 5/2011 | Kokoris et al. |
| 8,324,360 | B2 | 12/2012 | Kokoris et al. |
| 10,227,645 | B2 | 3/2019 | Craig |
| 10,351,908 | B2 | 7/2019 | Craig |
| 2009/0257950 | A1* | 10/2009 | Sligar et al. ............ A61P 31/12 514/23 |
| 2017/0260582 | A1* | 9/2017 | Boyanov et al. .... C12Q 1/6874 |
| 2017/0314062 | A1 | 11/2017 | Kokoris et al. |
| 2018/0230531 | A1* | 8/2018 | Ivanov et al. .... B01L 3/502738 |
| 2019/0039028 | A1 | 2/2019 | Wanunu et al. |

FOREIGN PATENT DOCUMENTS

| | | | | |
|---|---|---|---|---|
| CN | 108588199 A | 9/2018 | | |
| WO | 2014/072703 A1 | 5/2014 | | |
| WO | 2016/019030 A1 | 2/2016 | | |
| WO | 2016/069806 A2 | 5/2016 | | |
| WO | WO-2017004504 A1 * | 1/2017 | ......... G01N 33/6872 | |
| WO | 2018002125 A1 | 1/2018 | | |
| WO | WO-2018213372 A1 * | 11/2018 | ....... G01N 33/54353 | |
| WO | 2019166458 A1 | 9/2019 | | |

OTHER PUBLICATIONS

Stangl et al., "Detergent Properties Influence the Stability of the Glycophorin A Transmembrane Helix Dimer in Lysophosphatidylcholine Micelles," Biophys. J. 2012, 103(12):2455-2464. (Year: 2012).*

Inagaki, Sayaka et al., Biophysical characterization of membrane proteins in nanodiscs, Methods, vol. 59, pp. 287-300, 2013.

Wang, Yue et al., The evolution of nanopore sequencing, Frontiers in Genetics, vol. 5, Art. 449, 20 pp., 2015.

Bayburt, T. H., et al., Membrane protein assembly into Nanodiscs, FEBS Letters, 2010, pp. 1721-1727, 584 (9).

Denisov, I. G., et al., Directed Self-Assembly of Monodisperse Phospholipid Bilayer Nanodiscs with Controlled Size, J. Am. Chem. Soc., 2004, pp. 3477-3487, 126.

International Search Report and Written Opinion mailed Jan. 27, 2021 in connection with PCT/US2020/057970 filed Oct. 29, 2020, 12 pages.

Kim, B. N., et al., Parallel recordingofneurotransmittersreleasefro mchromaffincellsusing a 1010 CMOSICpotentiostatarraywithon-chipworkingelectrodes, Biosensors and Bioelectronics, 2013, pp. 736-744, 41.

Raschle, T., et al., Structural and Functional Characterization of the Integral Membrane Protein VDAC-1 in Lipid Bilayer Nanodiscs, J. Am. Chem. Soc., 2009, pp. 17777-17779, 131.

Stangl, M. et al., Detergent Properties Influence the Stability of the Glycophorin A Transmembrane Helix Dimer in Lysophosphatidylcholine Micelles, Biophysical Journal, Dec. 2012, pp. 2455-2464, 103.

* cited by examiner

*Primary Examiner* — Kaijiang Zhang

(74) *Attorney, Agent, or Firm* — Kristen K. Walker

(57) ABSTRACT

Methods and compositions for the manufacture and use of a detection apparatus based on one or more native biological nanopores are provided. Uses include, but are not limited to, detection and sequencing of nucleic acids.

4 Claims, 6 Drawing Sheets

METHODS AND COMPOSITIONS FOR ASSEMBLY OF BIOLOGICAL NANOPORES

CROSS-REFERENCE TO RELATED APPLICATION(S)

This patent application is a continuation of International Patent Application No. PCT/US2020/057970, filed Oct. 29, 2020, which claims priority to and the benefit of U.S. Provisional Application No. 62/928,207 filed Oct. 30, 2019. Each of the above patent applications is incorporated herein by reference as if set forth in its entirety.

FIELD OF THE INVENTION

The present invention relates generally to new methods and compositions for making protein-based nanopore sensors, more specifically, to methods of assembling native nanopore proteins in lipid nanodiscs, which are used as carriers to deliver the nanopore to a lipid membrane constituent of a sensor system, and to methods for the utilization thereof, particularly in nanopore-based nucleic acid sequencing methods.

BACKGROUND

In the last two decades, nanopore sensors have emerged as a powerful tool and have had a strong impact on science and biotechnology. Nanopore technology is commonly divided by its materials into biological nanopores and solid-state nanopores. Solid-state nanopores are conventionally fabricated by drilling a nanoscopic pore using semiconductor or microfluidic techniques like ion or electron bean sculpting in silicon or graphene-based membranes, such as Si, SiN, or $SiO_2$. However, most nanopore applications, such as DNA sequencing, small molecule sensing, drug screening, molecular sieving, and biomolecular analysis, require high-precision geometry, sensitivity, and reproducibility, which cannot be achieved with solid-state pores.

The most important and most highly desired application of nanopores is DNA sequencing. However, the major problems associated with the very high translocation speed of DNAs through nanopores (several nucleotides pass through the nanopore in a few micro seconds), result in few data points for each base, which hinders further analysis of data. To address such problems, Stratos Genomics has developed a method called Sequencing by Expansion ("SBX") that uses a biochemical process to transcribe the sequence of DNA onto a measurable polymer called an "Xpandomer" (see, e.g., Kokoris et al., U.S. Pat. No. 7,939,259, "High Throughput Nucleic Acid Sequencing by Expansion"). The transcribed sequence is encoded along the Xpandomer backbone in high signal-to-noise reporters that are separated by ~10 nm and are designed for high-signal-to-noise, well-differentiated responses. These differences provide significant performance enhancements in sequence read efficiency and accuracy of Xpandomers relative to native DNA. Xpandomers can enable several next generation DNA sequencing detection technologies and are well suited to nanopore sequencing.

α-Hemolysin (α-HL) is the most widely used biological nanopore for single-molecule analysis, mainly due to its small inner diameter and structural reproducibility. α-HL is a monomeric polypeptide that self-assembles in a lipid bilayer membrane to form a transmembrane heptameric pore, with a 2.6 nm-diameter vestibule and 1.5 nm-diameter limiting aperture (the narrowest point of the pore). The limiting aperture of the α-HL nanopore allows linear molecules, with dimensions on the order of that of single-stranded DNA, to pass through, or "translocate"; however molecules with a diameter larger the ~2.0 nm, such as double-stranded DNA, are precluded from translocation. Despite its advantages in DNA sequencing, α-HL (and other oligomeric, membrane-spanning protein nanopores) still has inherent structural limitations, due to, e.g., reduced stability of the native oligomer in aqueous solution and incomplete assembly of the native protein in a lipid membrane, giving rise to the need for improved methods and compositions for making biological nanopore sensors.

The present invention fulfills these needs and provides further related improvements advantages as discussed below.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

The details of one or more embodiments are set forth in the accompanying drawings and the description below. Other features, objects, and advantages will be apparent from the description and drawings, and from the claims.

In brief, the present disclosure provides methods and compositions for improved manufacture of nanopore-based sensors. In particular embodiments, the methods and compositions enable manufacture of biological nanopore-based sensors with improved assimilation of the native nanopore structure.

In one aspect, the invention provides a method of making a detection apparatus including one or more native nanopore proteins, including the steps of (a) forming an aqueous mixture including a nanopore protein, a membrane scaffold protein (MSP), and a first lipid to produce a sample of nanodisc-nanopore protein complexes, in which a population of the nanodisc-nanopore protein complexes in the sample each include a native nanopore protein; (b) providing a solid support including one or more apertures, in which a membrane is formed over each of the apertures, in which the membrane includes a second lipid, and in which the membrane separates a cis chamber from a trans chamber in the detection apparatus; and (c) and contacting the one or more membranes with the population of nanopore-nanodisc complexes including the native nanopore protein to assimilate a native nanopore protein into each of the membranes. In one embodiment, the method further includes the step of purifying the population of nanopore-nanodisc complexes including the native nanopore protein from the aqueous mixture prior to the step of contacting the one or more membranes with the population of nanopore-nanodisc complexes including the native nanopore protein. In a further embodiment, the step of purifying the population of nanopore-nanodisc complexes including the native nanopore protein includes one or both of size-exclusion chromatography and affinity chromatography. In another embodiment, the aqueous mixture further includes a detergent, in which the final concentration of the detergent is from about 14 mM to about 40 mM. In a further embodiment, the first lipid is 1,2-diphytanoyl-sn-glycero-3-phosphocholine (DPhPC), the MSP is MSP1D1, or a variant thereof, the nanopore protein is α-hemolysin (α-HL) or a variant thereof, the detergent is cholate, and the second lipid is 1,2-diphytanoyl-sn-glycero-3-phosphoethanolamine (DPhPE). In yet a further embodiment, the molar ratio of lipid to MSP to nanopore protein is about 101:6:1 or about 120:6:1. In another embodiment, the solid support includes a plurality of apertures, in which a membrane is formed over each of the plurality of apertures, and in which each of the membranes is contacted with the nanopore-nanodisc complex comprising the native nanopore protein.

In another aspect, the invention provides a method of sequencing a polymer including use of any of the above detection apparatus. In certain embodiments, the polymer is an Xpandomer.

In another aspect, the invention provides a method of forming a native nanopore protein in a membrane including the steps of (a) forming an aqueous mixture including a nanopore protein, a membrane scaffold protein (MSP), and a first lipid to produce a sample of nanodisc-nanopore protein complexes, in which a population of the nanodisc-nanopore protein complexes each includes a native nanopore protein; (b) providing a membrane including a second lipid; and (c) contacting the membrane with the population of nanopore-nanodisc complexes including the native nanopore protein to assimilate a native nanopore protein the membranes. In one embodiment, the method further includes the step of purifying the population of nanopore-nanodisc complexes including the native nanopore protein from the aqueous mixture prior to the step of contacting the membrane with the population of nanopore-nanodisc complexes including the native nanopore protein. In certain embodiments, the step of purifying the population of nanopore-nanodisc complexes includes one or both of size-exclusion chromatography and immobilized metal affinity chromatography. In another embodiment, the aqueous mixture further includes a detergent, wherein the final concentration of the detergent is from over 14 mM to 40 mM. In further embodiments, the first lipid is 1,2-diphytanoyl-sn-glycero-3-phosphocholine (DPhPC), the MSP is MSP1D1, or a variant thereof, the nanopore protein is α-hemolysin (α-HL) or a variant thereof, the detergent is cholate, and the second lipid is 1,2-diphytanoyl-sn-glycero-3-phosphoethanolamine (DPhPE). In yet another embodiment, the molar ratio of lipid to MSP to nanopore protein is about 101:6:1 or about 120:6:1.

In another aspect, the invention provides a composition including a nanopore-nanodisc complex in an aqueous buffer, in which the nanopore-nanodisc complex includes a native nanopore protein, a membrane scaffold protein (MSP), and a lipid and in which the aqueous buffer comprises a detergent. In one embodiment, the native nanopore protein is α-hemolysin (α-HL) or a variant thereof, the MSP is MSP1D1, or a variant thereof, the lipid is 1,2-diphytanoyl-sn-glycero-3-phosphocholine (DPhPC), and the detergent is cholate. In a further embodiment, the molar ratio of lipid to MSP to nanopore protein is about 101:6:1 or about 120:6:1 and the concentration of cholate is from over 14 mM to 40 mM.

In another aspect, the invention provides a composition including a lyophilized powder including a nanopore-nanodisc complex, in which the nanopore-nanodisc complex includes a native nanopore protein, a membrane scaffold protein (MSP), and a lipid. In one embodiment, the native nanopore protein is α-hemolysin (α-HL) or a variant thereof, the MSP is MSP1D1, or a variant thereof, and the lipid is 1,2-diphytanoyl-sn-glycero-3-phosphocholine (DPhPC). In a further embodiment, the molar ratio of lipid to MSP to nanopore protein is about 101:6:1 or about 120:6:1.

DETAILED DESCRIPTION OF THE INVENTION

Figure 1:
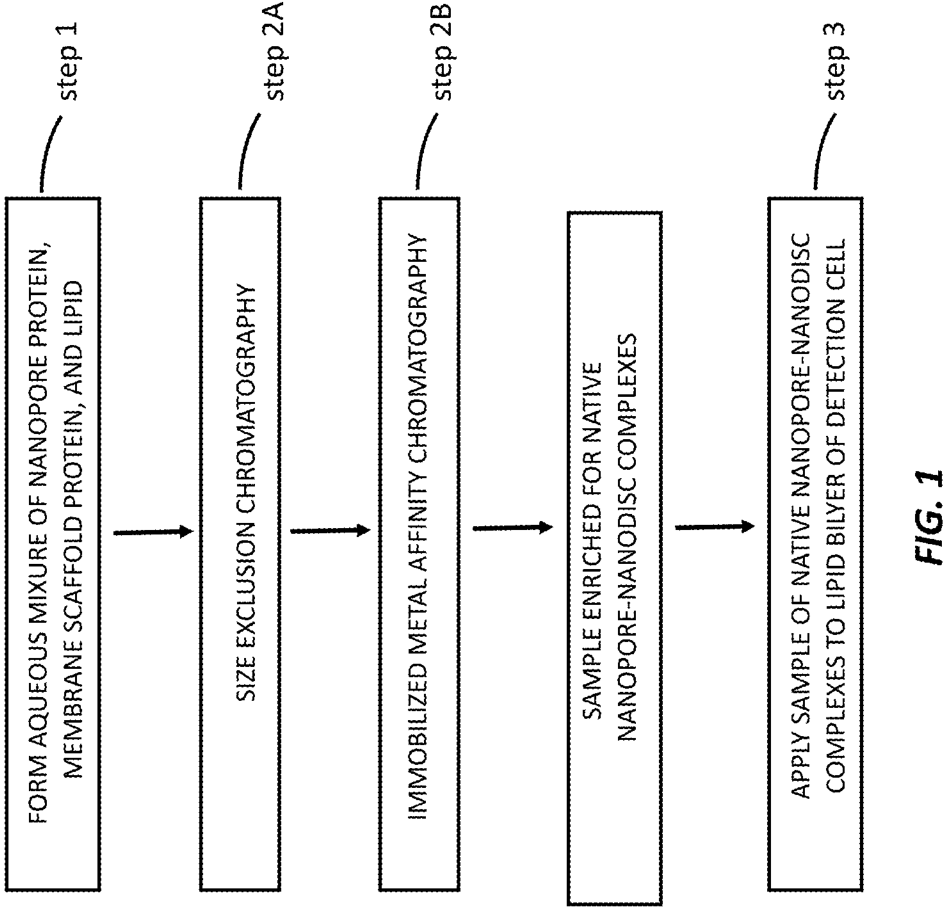
FIG. 1 is a flow chart illustrating one embodiment of a method of making a biological nanopore-based detection system.

The present invention may be understood more readily by reference to the following detailed description of preferred embodiments of the invention and the Examples included herein. Unless otherwise explained, all technical and scientific terms used herein have the same meaning as commonly understood by one of ordinary skill in the art to which this disclosure belongs.

Biological nanopore proteins that have found use in the nucleic acid sequencing arts include those based on natural transmembrane proteins that form pores when individual polypeptide subunits self-assemble in a membrane and oligomerize into their native higher-order structure. Conventional biological nanopore sensors, e.g., the αHL nanopore, are typically assembled by applying an aqueous solution of solubilized protein to a micron-sized membrane component of a detector system. To form a functional nanopore, the soluble protein subunits must insert into the membrane and correctly self-assemble to form the native higher-order structure. Reconstitution of native membrane proteins in lipid bilayers presents several technical challenges due to, e.g., low solubility and stability of the protein in aqueous solution and difficulty in efficiently and consistently assembling the proper native structure in a lipid substrate. The present disclosure addresses these challenges by providing methods and compositions for manufacturing nanopore sensors, whereby the native oligomeric nanopore structure is assembled in a lipid nanodisc prior to assimilating the nanopore in a membrane. Nanodiscs incorporating the native nanopore protein (e.g., complexes with the appropriate size and/or incorporation of a heterologous detection "tag") can be optionally purified from a mixture to provide a more homogenous sample of the native nanopore. The purified nanopore-nanodisc complexes can then be applied to a lipid bilayer membrane to allow for assimilation of the native protein structure into the membrane to form a functional nanopore sensor or detector. An additional advantage offered by the present invention is that the structure of the native nanopore protein is greatly stabilized when formed in a nanodisc, thus providing improved compositions for, e.g., storage and shipment of native nanopore proteins.

Nanodisc technology is well-known in the art. In some embodiments, nanodiscs are nanoscale discoidal phospholipid bilayers, which are stabilized and rendered soluble in aqueous solution by two encircling amphipathic helical protein "belts", termed membrane scaffold proteins (MSPs).

Nanodiscs can be used as a vehicle to incorporate membrane proteins (MP) of interest into the bilayer to preserve MP structure and activity and have been traditionally employed for biophysical, enzymatic or structural investigations of the MP (for review, see, e.g., Bayburt and Sligar, *FEBS Lett.;* 584(9): 1721-1727 (2010). In this approach, the membrane protein target and/or a phospholipid are transiently solubilized with a detergent in the presence of the encircling amphipathic helical MSP. When the detergent is removed, by dialysis or adsorbtion to hydrophobic beads, the target MP simultaneously assembles with phospholipids into a discoidal bilayer with the size controlled by the length of the MSP. The resultant nanodiscs thus keep membrane proteins in solution, provide a native-like phospholipid bilayer environment that provides stability and functional requirements of the incorporated target and also allow control of the oligomeric state of the target membrane protein. Nanodiscs are known to be robust and can be frozen or lyophilized with an incorporated MP. The inventors have found that nanodiscs offer several advantages as nanopore delivery and storage vehicles, as discussed further herein.

As used herein, the term "membrane scaffold protein" refers to a protein that can stabilize a phospholipid bilayer in a nanodisc by binding to the bilayer periphery. In general, membrane scaffold proteins have hydrophobic faces that can associate with the nonpolar interior of a phospholipid bilayer and hydrophilic faces that favorably interact with a polar solvent such as an aqueous buffer. Membrane scaffold protein sequences may be naturally occurring, or may be engineered using recombinant techniques or constructed de novo. Naturally occurring membrane scaffold proteins include apolipoproteins, which are components of lipoproteins. Known classes of apolipoproteins include: A (including, for example, apo A-I and apo A-II), B, C, D, E, and H. Non-naturally occurring membrane scaffold proteins include MSP1 and MSP2 described in U.S. Pat. No. 7,691,414, which is herein incorporated by reference in its entirety. An exemplary commercially available non-naturally occurring MSP is MSP1D1 available from, e.g., Sigma. The membrane scaffold proteins can be the full-length protein, or a truncated version of the protein. Membrane scaffold protein is not intended to encompass various functional membrane proteins including, but not limited to, ion channels and other transmembrane receptors, porins, certain cell adhesion molecules, and electron transport proteins such as NADH dehydrogenase and ATP synthases.

As used herein, the term "nanopore protein" refers to a polypeptide subunit and multimers of subunits that can create an aperture through a membrane when an appropriate higher-order structure is formed. Nanopore protein may refer to a single polypeptide subunit of a multimeric nanopore protein or different oligomeric forms of single polypeptide subunits. A "mixture of nanopore proteins" refers to a solution that may contain a heterogenous combination of single and/or oligomeric forms of a nanopore protein. "Native nanopore protein" refers to the natural, higher-order state of subunit oligomerization that can form a functional nanopore in a membrane. Exemplary nanopore proteins, i.e., biological nanopores, include α-hemolysin, *Mycobacterium smegmatis* porin A (MspA), aerolysin, phi29, gramicidin A, maltoporin, OmpG, OmpF, OmpC, *Vibrio cholerae* cytolysin, PhoE, Tsx, and F-pilus.

A preferred nanopore protein is α-hemolysin (α-HL). α-HL is the major cytotoxic agent released by bacterium *Staphylococcus aureus* and the first identified member of the pore forming beta-barrel toxin family. This toxin consists mostly of beta-sheets (68%) with only about 10% alpha-helices. The hla gene on the *S. aureus* chromosome encodes the 293 residue protein monomer, which forms heptameric oligomers in the cellular membrane to form a complete beta-barrel pore. The native α-HL nanopore protein is thus an assembly, i.e. oligomer, of seven α-HL protein monomers.

Conventional biological mutagenesis can be used to optimize any protein constituent of the nanopore-nanodisc complex for use in a composition or method set forth herein. In some embodiments, the process of isolating a nanodisc-nanopore complex can benefit from a polyhistidine affinity tag (i.e., "His-tag") joined to either the MSP or nanopore protein, which is used for purification of the complex over an immobilized metal affinity column (e.g., over a nickel affinity column) α-HL or MSP with a terminal 6× His tag can be expressed, reconstituted and purified as demonstrated by a SDS-PAGE gel. Biological functionality of the purified His-tagged proteins is expected to be similar to that of a non-tagged protein. Other mutations can also be introduced for purification purposes. For example, a cysteine moiety can be introduced into the protein sequence by mutagenesis and used for chemical conjugation to thiol reactive moieties (e.g. maleimides or iodoacetamides) of affinity tags. Exemplary affinity tags include biotin (which can mediate purification via solid-phase streptavidin), DNA and RNA (which can mediate purification via solid-phase nucleic acids having complementary sequences), epitopes (which can mediate purification via solid-phase antibodies or antibody fragments) or other ligands (which can mediate purification via solid-phase receptors for those ligands).

Protein engineering and mutagenesis techniques can be used to alter the structure of biological pores and tailor their properties for specific applications. In certain embodiments, α-hemolysin may be mutated to generate variants with improved stability and/or with altered surface charge, e.g., within the interior of the pore to optimize detection of analytes of interest. Suitable α-HL variants include those disclosed in published PCT applications WO2016069806, WO2018002125, and WO2019166458 and U.S. Pat. Nos. 15,274,770 and 10,351,908, which are incorporated herein by reference. In certain embodiments, suitable α-HL variants may include one or more of the following mutations: A1K/R, D2N, S3K, D4K/N, K8R, T12K/R, N17K/R, D24A, V26D, H35D/E/G/L, K37S, N47K, E70K, S99K, Y101D, S106K, T109K, E111N/S, M113A/S, D127G, D128G/K, T129G, T131G, L1351, T145S, K147N/S, V149K, P151K, T233R, E287R, and M298A.

As used herein, a "membrane" is a component of a sensor or detection system or apparatus and is not a component of the nanopore-nanodisc complex. The membrane is a thin film that separates two compartments or reservoirs (e.g., a cis chamber and a trans chamber) and prevents the free diffusion of ions and other molecules between these. Suitable membranes are amphiphilic layers formed of amphiphilic molecules, i.e., molecules possessing both hydrophilic and lipophilic properties. Such amphiphilic molecules may be either naturally occurring, such as phospholipids, or synthetic. Exemplary amphiphilic materials include various phospholipids such as 1,2-diphytanoyl-sn-glycero-3-phosphoethanolamine (DPhPE), palmitoyl-oleoyl-phosphatidylcholine (POPC), dioleoyl-phosphatidyl-methylester (DOPME), 1,2-diphytanoyl-sn-glycero-3-phosphatidylcholine (DPhPC) dipalmitoylphosphatidylcholine (DPPC), phosphatidylcholine, phosphatidylethanolamine, phosphatidylserine, phosphatidic acid, phosphatidylinositol, phosphatidylglycerol, and sphingomyelin. Exemplary synthetic amphiphilic molecules include such molecules as poly(n- butyl methacrylate-phosphorylcholine), poly(ester amide)-phosphorylcholine, polylactide-phosphorylcholine, polyethylene glycol-poly(caprolactone)-di- or tri-blocks, polyethylene glycol-polylactide di- or tri-blocks and polyethylene glycol-poly(lactide-glycolide) di- or tri-blocks.

Preferably, the membrane is a lipid bilayer. Lipids bilayers are models of cell membranes and have been widely used for experimental purposes. A membrane can also be a solid-state membrane, i.e., a layer prepared from solid-state materials in which one or more aperture is formed. The membrane may be a layer, such as a coating or film on a supporting substrate, or it may be a free-standing element. Examples of materials used for thin film solid state membranes include silicon nitride, aluminum oxide, titanium oxide, and silicon oxide.

FIG. 1 summarizes three basic steps of an exemplary method for forming a nanopore sensor component of a detection apparatus according to the present invention; details of each step are discussed further herein. In step 1, an aqueous mixture of nanopore protein, a suitable lipid, and a suitable membrane scaffold protein is formed to provide a sample of nanopore-nanodisc complexes. In one embodiment, the nanopore is α-HL, the suitable lipid is DPhPC, and the membrane scaffold protein is MSPD1. This sample includes a population of nanopore-nanodisc complexes that each contain a native nanopore protein; however, not every complex in the sample will necessarily include the properly assembled native nanopore protein, thus, in certain embodiments, the sample may be described as a "heterogenous sample" and it may be advantageous to perform one or more purification steps to provide a sample enriched for the nanopore-nanodisc complexes of interest. In steps 2A and 2B, nanopore-nanodisc complexes with the appropriate physical properties may optionally be isolated or purified from the aqueous mixture. In this embodiment, two sequential purification steps are performed: size-exclusion chromatography (SEC, step 2A) and Immobilized Metal Affinity Chromatography (IMAC, step 2B). The purification step(s) enrich for a population of nanopore-nanodisc complexes that include the native nanopore protein. It is to be understood that any suitable purification protocol known in the art may be employed according to the methods described herein. In step 3, the purified nanopore-nanodisc complexes are applied to the lipid bilayer component, i.e., membrane, of a detection cell to enable assimilation of the native nanopore protein into the membrane to form a functional nanopore sensor. Advantageously, according to this methodology, a sample enriched for the native, oligomeric protein is applied to the membrane, thus increasing the efficiency of forming a functional sensor. In contrast, prior art methodologies require correct in-membrane self-assembly of protein subunits to form the native higher-order structure, which is a less efficient and potentially error-prone process that can compromise functionality of the detection system.

In certain embodiments, a nanopore-nanodisc complex can be, for example, a 7 to 16 nm diameter lipid bilayer disc that is stabilized by a membrane scaffold protein (MSP). In some embodiments, the MSP is a suitable derivative of apoA-I, such as the commercially available MSP1D1 protein. Other types of amphipathic nanodisc "belts" are contemplated by the present invention, such as amphipathic peptides. It will be understood that a nanopore-nanodisc complex can have a diameter that is smaller than 7 nm (e.g., smaller than 6 nm, 5 nm, 4 nm, 2 nm or less in diameter) or larger than 16 nm (e.g., larger than 18 nm, 20 nm, or 25 nm or greater in diameter). Typically, the area of lipid disc used in a method or composition set forth herein is no greater than about 50,000 $nm^2$ or in some cases no greater than about 10,000 $nm^2$ or sometimes no greater than about 1,000 $nm^2$ or even other times no greater than about 500 $nm^2$. A nanopore-nanodisc complex can, but need not necessarily, occupy a circular area. In particular conditions, a nanopore-nanodisc complex can be distinguished from a vesicle or liposome due to the absence of an aqueous lumen for the nanodisc and can be distinguished from a micelle due to the presence of a bilayer in the nanodisc. It will be understood that a nanopore-nanodisc complex can be made from other materials as well. For example, a nanodisc can be formed from a non-lipid membrane. One of skill in the art will appreciate that the optimal physical properties of a nanodisc will be determined by the particular application(s) of interest, e.g., the physical properties of the target protein and other components of the system to which the target protein is incorporated. For example, nanodiscs incorporating a nanopore protein should have a size suitable to preserve the membrane solubility and transmembrane pore structure of the native protein when the nanopore-nanodisc assembly is applied to a lipid bilayer. In certain embodiments, in which nanodiscs are assembled with DPhPC, MSP1D1, and α-HL the complexes are expected to be about 9.7 nm in diameter and around 4.6 to 5.6 nm thick.

As described herein, the lipid nanodisc may be composed of a bilayer of lipid molecules surrounded by two parallel belt-like MSPs, in which the amphipathic helices of the MSPs stabilize the hydrophobic fatty acid on the edge of the lipid disc. Particularly useful lipid nanodiscs and compositions and methods for their manufacture are set forth, for example, in U.S. Pat. Nos. 7,083,958 and 7,662,410, which are incorporated herein by reference. In certain embodiments of the present invention, useful lipids for formation of nanodiscs include 1,2-diphytanoyl-sn-glycero-3-phosphocholine (DPhPC) and 1,2-dimyristoyl-sn-glycero-3-phosphocholine (DMPC).

In certain embodiments, lipid nanodiscs may be prepared by mixing MSP with detergent stabilized phospholipid. Self-assembly of nanodiscs occurs during removal of the detergent from the mixture, as described herein. It has been demonstrated that the presence of MSP confines the shape and size of the lipid nanodisc and provides a narrow size distribution (+/−3%), excellent reproducibility and exceptional stability in detergent-free aqueous solution. The ratio of MSP to detergent can be selected to achieve desired size and characteristics of the nanodiscs. For example, the number of structural units of the MSP can be varied to allow the nanodisc diameter to be tuned from 9.8 nm to 12.9 nm as set forth in Denisov et al., J. Am. Chem. Soc. 126, 3477-3487 (2004), which is incorporated herein by reference. Exemplary methods for incorporating membrane proteins into nanodiscs are set forth in Raschle et al., J. Am. Chem. Soc. 131, 17777-17779 (2009). Similar methods can be used to insert protein nanopores, such as α-HL, MspA, aerolysin and others into lipid nanodiscs. In some embodiments, nanopore-nanodisc complexes are formed in an aqueous buffer composed of 20 mM Tris, pH 7.4, 0.5M EDTA, 100 mM NaCl, and from 14 mM to 40 mM cholate. In certain embodiments, the buffer contains 19 mM cholate. In some embodiments, DPhPC lipid is added to the aqueous mixture in a solution containing 50 mM DPhPC, 20 mM Tris, pH 7.4, and 100 mM sodium cholate. In some embodiments, the final concentration of cholate in the nanodisc assembly reaction is greater than about 14 mM; in one specific embodiment, the final concentration of cholate is about 19 mM.

In particular embodiments, nanopore-nanodisc complexes form in a mixture of membrane scaffold protein (MSP), detergent-solubilized phospholipid (e.g., DPhPC), and nanopore protein. In the mixture, MSP self-assembles with detergent-solubilized phospholipid to form nanodiscs that embed the α-HL nanopore protein. The self-assembly occurs as the detergent is removed from the mixture, for example, using Bio-Beads®. (Bio-Rad, Hercules Calif.). In some embodiments, the molar ratio of nanopore protein to MSP protein to lipid will be (from about 0.5 to about 5) to (from about 1 to about 15) to (from about 50 to about 200). The optimal ratio may be determined empirically and will depend on the particular protein and lipid constituents of the complexes of interest, as well as the particular method of forming the nanodisc complex. In one exemplary embodiment, the molar ratio of α-HL protein to MSP1D1 protein to DPhPC lipid is about 1 to 6 to 120 (i.e., 1:6:120). In another embodiment, the molar ratio of α-HL protein to MSP1D1 protein to DPhPC lipid is about 1:6:101, A population of nanopore-nanodisc complexes containing the native nanopore protein may be purified from a mixture by conventional size-exclusion chromatography (SEC), which is well known in the art. The size of the nanopore-nanodisc complex of interest will determine the properties and details of the column and chromatography protocol. In one embodiment, the nanopore-nanodisc complexes of interest are collected using a column designed to purify complexes with a $M_r$ of ~10,000-600,000. Methods known in the art (e.g., gel electrophoresis and Western blotting) can be used to confirm that the proper fractions are being retained from the SEC column eluate. In certain embodiments, an additional purification step is employed to further enrich for nanopore-nanodisc complexes containing the native nanopore protein. For example, immobilized metal affinity chromatography (e.g., a nickel-based affinity matrix) may be used to specifically retain complexes in which either the MSP or nanopore protein has been engineered to express a polyhistidine affinity tag. Such methodologies are well-described in the art.

The nanopore-nanodisc complexes described herein demonstrate improved stability in aqueous buffers and can also be lyophilized, e.g., for storage and shipment, and reconstituted as required, e.g., for use in forming a nanopore sensor or detection system. As used herein, the term "buffer" refers to an aqueous solution capable of maintaining the pH of the solution at a nearly constant value. The buffer accomplishes this by including a weak acid and its conjugate base, such that the pH does not substantially change following addition of a small amount of acid or base. Representative buffering agents include citric acid, acetic acid, dipotassium phosphate ($K_2HPO_4$), N-cyclohexyl-2-aminoethanesulfonic acid (CHES), and borate. Buffers commonly used include, but are not limited to, TAPS, bicine, tris, tricine, TAPSO, HEPES, TES, MOPS, PIPES, cacodylate, SSC, MES and succinic acid. In some embodiments, the nanopore-nanodisc complexes can be stored in an aqueous buffer at 4° C.

The nanopore-nanodisc complexes described herein may be components of a composition. The components may, for example, be dried (e.g., powder) or in a stable buffer (e.g., chemically stabilized, thermally stabilized). Dry components may, for example, be prepared by lyophilization, vacuum and centrifugal assisted drying and/or ambient drying. In various embodiments, the compositions including the nanopore-nanodisc complexes are in lyophilized form in a single container. In other embodiments, the composition is an aqueous solution that includes the nanopore-nanodisc complexes that is stable when stored at 4° C.

The term "lyophilize" as used herein in connection with the formulation according to the invention denotes a process in which a composition is stabilized by freeze-drying methods known in the art. The solvent (e.g. water) is removed by freezing following sublimation under vacuum and desorption of residual water at elevated temperature. In the pharmaceutical field, the lyophilized compositions usually has a residual moisture of about 0.1 to 5% (w/w) and is present as a powder or a physical stable cake. The lyophilisate is characterized by a fast dissolution after addition of a reconstitution medium.

The term "reconstituted formulation" as used herein denotes a formulation which is lyophilized and re-dissolved by addition of a diluent. The diluent can contain, without limitation, water, sodium chloride solutions (e.g. 0.9% (w/v) NaCl), glucose solutions (e.g. 5% glucose), surfactant containing solutions (e.g. 0.01% polysorbate 20 or polysorbate 80), a pH-buffered solution (e.g. phosphate-buffered solutions) and combinations thereof.

The present disclosure provides use of the nanopore-nanodisc complexes described herein in the manufacture of a system for data acquisition (e.g., a sensor or detection apparatus). In an exemplary system, a lipid bilayer membrane is formed across an aperture in a, e.g., PTFE, solid-support cell. The lipid bilayer membrane may be formed according to the following steps: i) priming the support cell with a thin coat of lipid (e.g., 1,2-diphytanoyl-sn-glycero-3-phosphoethanolamine, "DPhPE") dissolved in hexane, ii) air-drying the painted cell to remove the hexane iii) painting lipid over the support cell by dissolving PE in 1-hexadecene and depositing the solution over the primed support cell with a pipette and iv) moving an air bubble over the aperture in the support cell to form a lipid bilayer membrane over the aperture. To insert the nanopore into the membrane, the nanopore-nanodisc complex is applied to the lipid-bilayer membrane, whereupon the nanopore protein assimilates (i.e., inserts) into the membrane. In certain embodiments, the native nanopore is inserted into the membrane by mechanical force, e.g., by electroporation or by using bubbles.

The detection system includes a membrane that separates a cis chamber and a trans chamber. Standard, e.g., Ag/AgCl, electrodes on the cis and trans side of the nanopore provide a current source. Use of a current sensing circuit measures the ion current that passes through the nanopore in a solution containing a suitable electrolyte, e.g., >1M KCl, between the two ion sensitive electrodes. The electrodes complete the circuit through a transimpedance amplifier, which provides a voltage output proportional to the ion current across a frequency range. Data from the nanopore can be acquired with an Axopatch 200B amplifier. This type of system is consistent with conventional systems used to evaluate analytical capabilities in the nanopore art. Assimilation of the native nanopore protein into the membrane produces the functional sensor that enables current to flow across the membrane. In this manner, proper assimilation of a native nanopore protein into the membrane can be detected by monitoring ionic current in the system, for example, the expected current at −100 mV may be ~200 pA upon correct assimilation of a native nanopore.

In some embodiments, a detection system may include an array of nanopores with any suitable number of nanopores. In some instances, the array includes about 200, about 400, about 600, about 800, about 1000, about 1500, about 2000, about 3000, about 4000, about 5000, about 10,000, about 15,000, about 20,000, about 40,000, about 60,000, about 80,000, about 100,000, about 200,000, about 400,000, about 600,000, about 800,000, about 1,000,000, and the like nanopores. In some instances, the array includes at least 200, at least 400, at least 600, at least 800, at least 1000, at least 1500, at least 2000, at least 3000, at least 4000, at least 5000, at least 10,000, at least 15,000, at least 20,000, at least 40,000, at least 60,000, at least 80,000, at least 100,000, at least 200,000, at least 400,000, at least 600,000, at least 800,000, or at least 1,000,000 nanopores in proximity to a sensor circuit or sensing electrodes. The one or more nanopore may be associated with an individual electrode and sensing integrated circuit or a plurality of electrodes and sensing integrated circuits. In some embodiments, an array of transimpedance amps implemented in CMOS are arranged to measure an array of independent sensor currents in parallel. An example of such an amplifier array has been disclosed by Kim et al. (see, e.g., Kim, B. N., Herbst, A. D., Kim, S. J., Minch, B. A., & Lindau, M. 2013. Parallel Recording of Neurotransmitters Release from Chromaffin Cells using a 10×10 CMOS IC Potentiostat Array with On-Chip Working Electrodes. Biosensors and Bioelectronics, 41, 736-744). A nanopore device may include a plurality of individually addressable sensing electrodes. Each sensing electrode can include a membrane adjacent to the electrode, and one or more nanopores in the membrane.

In particular embodiments, each of the lipid nanodiscs that is applied to a membrane of an array set forth herein will have no more than one protein nanopore assimilated therein. Alternatively, individual nanodiscs can include more than one protein nanopore.

A detection apparatus of the present disclosure can be used to detect any of a variety of analytes including, but not limited to, ions, nucleic acids, nucleotides, polypeptides, biologically active small molecules, lipids, sugars or the like. Accordingly, one or more of these analytes can be present in or passed through the aperture of a protein nanopore in an apparatus set forth herein.

In preferred embodiments, the present disclosure further provides systems and methods for sequencing nucleic acids based on "Sequencing by Expansion". The Sequencing by Expansion (SBX) protocol, developed by Stratos Genomics (see, e.g., Kokoris et al., U.S. Pat. No. 7,939,259, "High Throughput Nucleic Acid Sequencing by Expansion") is based on the polymerization of non-natural monomeric substrates known as "XNTPs". In general terms, SBX uses this biochemical polymerization to transcribe the sequence of a DNA template onto a measurable polymer called an "Xpandomer". The transcribed sequence is encoded along the Xpandomer backbone in high signal-to-noise reporters that are separated by ~10 nm and are designed for high-signal-to-noise, well-differentiated responses. These differences provide significant performance enhancements in sequence read efficiency and accuracy of Xpandomers relative to natural DNA. A generalized overview of the SBX process is depicted in FIGS. 2A, 2B, 2C and 2D.

Figure 2A:
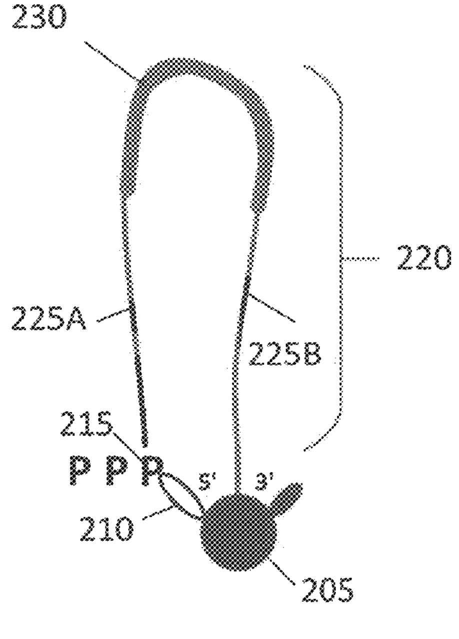
FIGS. 2A, 2B, 2C and 2D are condensed schematics illustrating the main features of a generalized XNTP and their use in Sequencing by Expansion (SBX).

XNTPs are expandable, 5' triphosphate modified non-natural substrates compatible with template dependent enzymatic polymerization. A highly simplified XNTP is illustrated in FIG. 2A, which emphasizes the unique features of these non-natural substrates: XNTP 200 has two distinct functional regions; namely, a selectively cleavable phosphoramidate bond 210, linking the 5' α-phosphate 215 to the nucleobase 205, and a tether 220 that is attached within the nucleoside triphosphoramidate at positions that allow for controlled expansion by cleavage of the phosphoramidate bond. The tether of the XNTP is comprised of linker arm moieties 225A and 225B separated by the selectively cleavable phosphoramidate bond. Each linker attaches to one end of a reporter construct 230 via a linking group (LG), as disclosed in U.S. Pat. No. 8,324,360 to Kokoris et al., which is herein incorporated by reference in its entirety. XNTP 200 is illustrated in the "constrained configuration", characteristic of the XNTP substrates and the daughter strand following polymerization. The constrained configuration of polymerized XNTPs is the precursor to the expanded configuration, as found in Xpandomer products. The transition from the constrained configuration to the expanded configuration occurs upon scission of the P-N bond of the phosphoramidate within the primary backbone of the daughter strand.

Figure 2B:
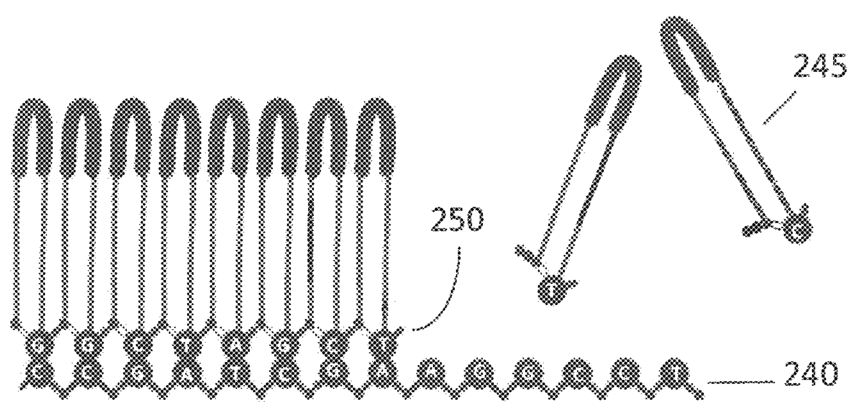
Figure 2C:
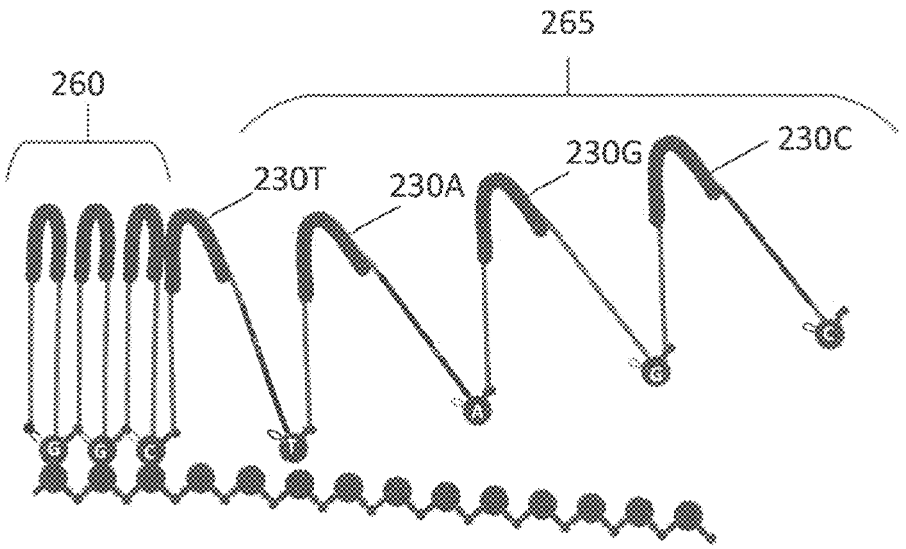

Synthesis of an Xpandomer polymer is summarized in FIGS. 2B and 2C. During assembly, the monomeric XNTP substrates 245 (XATP, XCTP, XGTP and XTTP) are polymerized on the extendable terminus of a nascent daughter strand 250 by a process of template-directed polymerization using single-stranded template 240 as a guide. Generally, this process is initiated from a primer and proceeds in the 5' to 3' direction. Generally, a DNA polymerase or other polymerase is used to form the daughter strand, and conditions are selected so that a complimentary copy of the template strand is obtained. After the daughter strand is synthesized, the coupled tethers comprise the constrained Xpandomer that further comprises the daughter strand. Tethers in the daughter strand have the "constrained configuration" of the XNTP substrates. The constrained configuration of the tether is the precursor to the expanded configuration, as found the Xpandomer product.

As shown in FIG. 2C, the transition from the constrained configuration 260 to the expanded configuration 265 results from cleavage of the selectively cleavable phosphoramidate bonds (illustrated for simplicity by the unshaded ovals) within the primary backbone of the daughter strand. In this embodiment, the tethers comprise one or more reporters or reporter constructs, 230A, 230C, 230G, or 230T, specific for the nucleobase to which they are linked, thereby encoding the sequence information of the template. In this manner, the tethers provide a means to expand the length of the Xpandomer and lower the linear density of the sequence information of the parent strand.

Figure 2D:
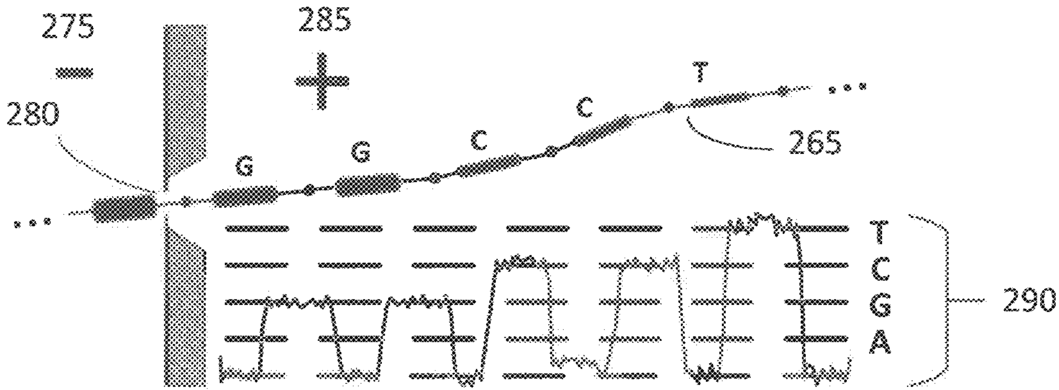

FIG. 2D illustrates an Xpandomer 265 translocating through a nanopore 280, from the cis reservoir 275 to the trans reservoir 285. As illustrated in FIG. 1, an α-HL nanopore-nanodisc assembly is assimilated into a lipid bilayer membrane which separates and electrically isolates the two reservoirs of electrolytes. A typical electrolyte has 1 molar KCl buffered to a pH of 7.0. The α-HL nanopore is oriented to capture the Xpandomer from the stem side first. This orientation is advantageous using a translocation control method because it causes fewer blockage artifacts then occur when entering vestibule first. When a small voltage, typically 100 mV, is applied across the bilayer, the nanopore constricts the flow of ion current and is the primary resistance in the circuit. Upon passage through the nanopore, each of the reporter construct of the linearized Xpandomer (in this illustration, labeled "G", "C" and "T") generates a distinct and reproducible electronic signal (illustrated by superimposed trace 290), specific for the nucleobase to which it is linked.

EXAMPLES

Example 1

Assembly and Purification of an a-Hemolysin Nanopore in a Nanodisc Carrier

Nanodisc Formation.

This Example describes reconstitution of the native α-hemolysin nanopore protein in lipid nanodiscs and purification of the nanopore-nanodisc complexes for assimilation of the native nanopore protein in a lipid membrane.

Nanopore-nanodisc complexes were formed by incubating α-hemolysin protein, MSP protein, and DPhPC lipid together at a molar ratio of 1:6:101. The reaction buffer was composed of 20 mM Tris, pH 7.4, 0.5 mM EDTA, 100 mM NaCl, and 30 mM cholate. Wildtype α-hemolysin protein was obtained from Sigma and a stock solution of 20 μM (calculated for the heptameric form) was prepared in 50% glycerol/50% water. A 50 mM stock solution of DPhPC (available from Avanti Polar Lipids) was prepared in 20 mM Tris, pH 7.4 supplemented with 100 mM sodium cholate. MSP1D1 protein (with an N-terminal his-tag) was obtained from Sigma and a 202 μM stock solution was prepared, as per the manufacturer's instructions. The 134 μL nanodisc assembly mixture included 0.675 mM DPhPC, 6.67 μM α-HL, and 40 μM MSP. The final concentration of cholate was determined to be >14 mM, which the inventors have found to be preferable for assembly of α-HL/DPhPC/MSP nanodisc complexes. The assembly mixture was incubated for 60 minutes at room temperature. To remove the detergent, 78.8 mg of biobeads SM-2 (available from BioRad) was added and the mixture was shaken at 1200 rpm for 2.5 hrs at room temperature. The beads were removed by passing the mixture through a 45μ filter.

Nanopore-Nanodisc Complex Purification.

To isolate nanopore-nanodiscs complexes containing the native heptameric α-HL protein, size exclusion chromatography (SEC) was first performed using a Superdex 200 Increase column (commercially available from GEH) that was selected based on the predicted size of the complexes of interest. The column was equilibrated with MSP buffer (20 mM Tris, pH 7.4, 100 mM NaCl, and 0.5 mM EDTA) then the 105 μL nanodisc assembly mixture was added and the flow rate was adjusted to 0.5 mL/min at 160 psi. The column trace is shown in FIG. 13, with the two fractions collected denoted as "1" and "2". The presence of heptameric α-HL protein in fraction 2 was confirmed by gel electrophoresis.

Next, a Ni-NTA purification step was performed. The column resin (commercially available from Qiagen) was prepared by adding 50 μL resin to an empty Ni-NTA spin column and the column was spun at 700×g for two minutes to remove the storage buffer. The column was then equilibrated with 400 μL EQ buffer containing 20 mM Tris, pH 7.5 and 10 mM imidazole. The EQ buffer was removed by spinning the column at 700×g for two minutes. The F2 nanodisc sample was then added to the column and the column contents were mixed by securing the column on an end-over-end rotator for 15 minutes. The column was the centrifuged at 700×g for two minutes and washed three times with 700 μL of wash buffer containing 20 mM Tris, pH 7.5 and 25 mM imidazole. The His-tagged protein/nanodisc assemblies were then eluted by adding 150 μL of a buffer containing 20 mM Tris, pH 7.5 and 250 mM imidazole. The column was incubated for 5 minutes then eluate was collected by centrifuging the column at 700×g for two minutes.

Figure 3:
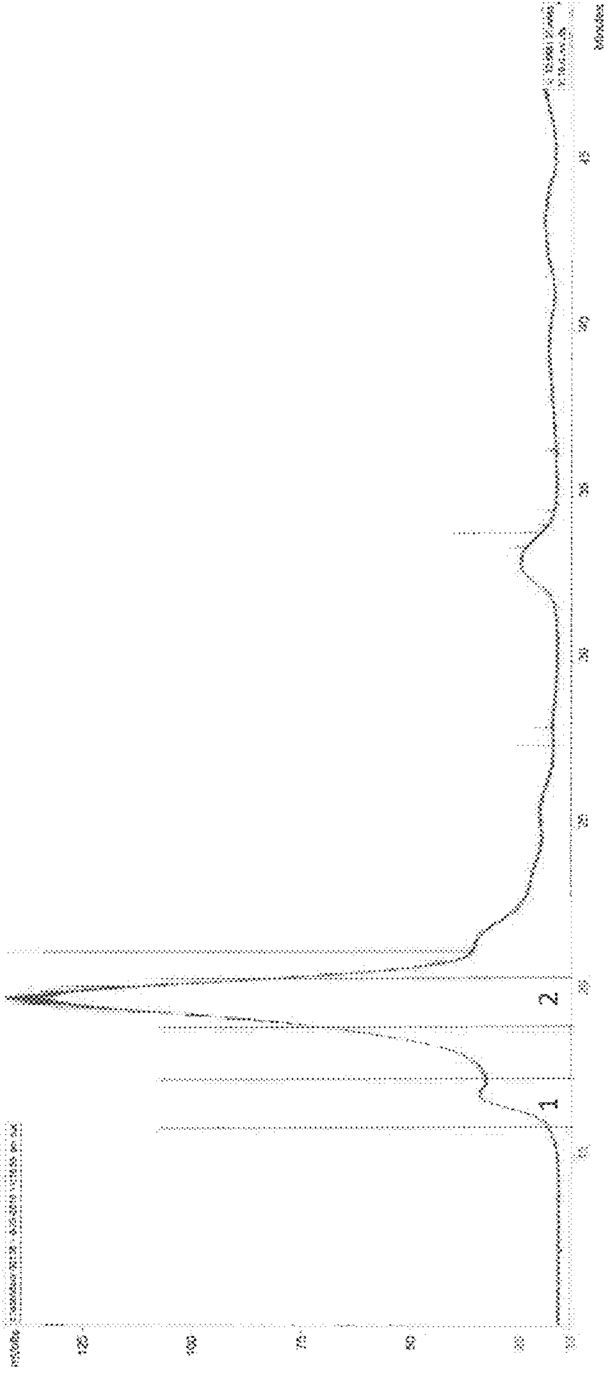
FIG. 3 is a SEC trace showing the A280 of eluted sample over time.
Figure 4:
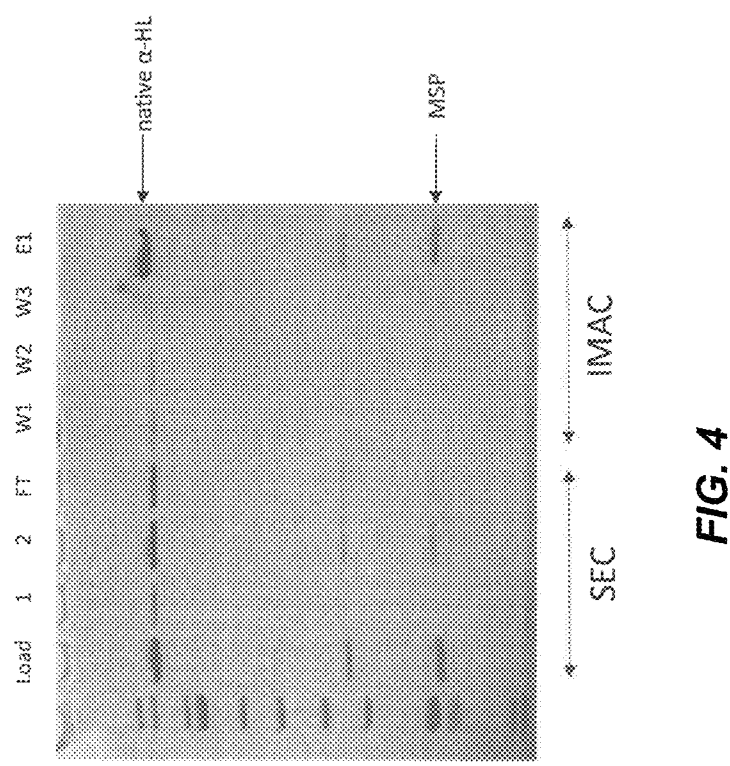
FIG. 4 is a gel showing samples of protein taken from various stages of a nanopore purification process.

The efficacy of the purification steps were monitored and assessed by analysis of the following samples by gel electrophoresis: load sample (1 μL of the sample applied to the SEC column); sample 1 (15 μL of fraction 1 collected from the SEC column at 16:30-17:55); sample 2 (15 μL of fraction 2 collected from the SEC column at 19:00-20:45); FT sample (15 μL of the column flow through); samples W1, W2, and W3 (15 μL each of the first, second, and third wash samples from the IMAC; and sample E1 (15 μL of the sample eluted off the IMAC). A representative gel is shown in FIG. 3. Arrows indicate the position of the heptameric α-HL protein and the MSP protein. These results confirm successful assembly and purification of α-HL nanopore-nanodisc complexes containing the native nanopore protein. A faint band on the gel representing monomeric α-HL protein may be the result of dissociation of the native heptameric oligomer as the protein sample is run in the gel.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and Applicants reserve the right to revise the application or claims to refer specifically to any individual member or any subgroup of members of the Markush group.

It is to be understood that the terminology used herein is for the purpose of describing specific embodiments only and is not intended to be limiting. It is further to be understood that unless specifically defined herein, the terminology used herein is to be given its traditional meaning as known in the relevant art.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents, i.e., one or more, unless the content and context clearly dictates otherwise. For example, the term "a sensor" refers to one or more sensors, and the term "a detection apparatus comprising a sensor" is a reference to a detection apparatus that includes at least one sensor, where the detection apparatus comprising a sensor may have, for example, 1 sensor, 10 sensors, $10^2$ sensors, $10^3$ sensors, $10^4$ sensors, $10^5$ sensors, $10^6$ sensors or more than $10^6$ sensors. A plurality of sensors refers to more than one sensor. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

Any headings used within this document are only being utilized to expedite its review by the reader, and should not be construed as limiting the invention or claims in any manner Thus, the headings and Abstract of the Disclosure provided herein are for convenience only and do not interpret the scope or meaning of the embodiments.

Where a range of values is provided herein, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet, including but not limited to, U.S. Provisional Patent Application No. 62/928,207, filed on Oct. 30, 2019, are incorporated herein by reference, in their entirety. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

SPECIFICALLY INCLUDED EMBODIMENTS

The following embodiments are specifically contemplated as part of the disclosure. This is not intended to be an exhaustive listing of potentially claimed embodiments included within the scope of the disclosure.

Embodiment 1. A method of making a detection apparatus comprising one or more native nanopore proteins, comprising the steps of:

(a) forming an aqueous mixture comprising a nanopore protein, a membrane scaffold protein (MSP), and a first lipid to produce a sample of nanodisc-nanopore protein complexes, wherein a population of the nanodisc-nanopore protein complexes in the sample each comprise a native nanopore protein;

(b) providing a solid support comprising one or more apertures, wherein a membrane is formed over each of the apertures, wherein the membrane comprises a second lipid, and wherein the membrane separates a cis chamber from a trans chamber in the detection apparatus; and (c) contacting the one or more membranes with the population of nanopore-nanodisc complexes comprising the native nanopore protein to assimilate a native nanopore protein into each of the membranes.

Embodiment 2. The method of embodiment 1, further comprising the step of purifying the population of nanopore-nanodisc complexes comprising the native nanopore protein from the aqueous mixture prior to the step of contacting the one or more membranes with the population of nanopore-nanodisc complexes comprising the native nanopore protein.

Embodiment 3. The method of embodiment 2, wherein the step of purifying the population of nanopore-nanodisc complexes comprising the native nanopore protein comprises one or both of size-exclusion chromatography and affinity chromatography.

Embodiment 4. The method of embodiment 1, wherein the aqueous mixture further comprises a detergent, wherein the final concentration of the detergent is from about 14 mM to about 40 mM.

Embodiment 5. The method of embodiment 4, wherein the first lipid is 1,2-diphytanoyl-sn-glycero-3-phosphocholine (DPhPC), the MSP is MSP1D1, or a variant thereof, the nanopore protein is α-hemolysin (α-HL) or a variant thereof, the detergent is cholate, and the second lipid is 1,2-diphytanoyl-sn-glycero-3-phosphoethanolamine (DPhPE).

Embodiment 6. The method of embodiment 5, wherein the molar ratio of lipid to MSP to nanopore protein is about 101:6:1 or about 120:6:1

Embodiment 7. The method of embodiment 1, wherein the solid support comprises a plurality of apertures, wherein a membrane is formed over each of the plurality of apertures, and wherein each of the membranes is contacted with the nanopore-nanodisc complex comprising the native nanopore protein.

Embodiment 8. A method of sequencing a polymer comprising use of the detection system of any of embodiments 1-7.

Embodiment 9. The method of embodiment 8, wherein the polymer is an Xpandomer.

Embodiment 10. A method of forming a native nanopore protein in a membrane comprising the steps of:

(a) forming an aqueous mixture comprising a nanopore protein, a membrane scaffold protein (MSP), and a first lipid to produce a sample of nanodisc-nanopore protein complexes, wherein a population of the nanodisc-nanopore protein complexes each comprise a native nanopore protein;

(b) providing a membrane comprising a second lipid; and (c) contacting the membrane with the population of nanopore-nanodisc complexes comprising the native nanopore protein to assimilate a native nanopore protein the membranes.

Embodiment 11. The method of embodiment 10, further comprising the step of purifying the population of nanopore-nanodisc complexes comprising the native nanopore protein from the aqueous mixture prior to the step of contacting the membrane with the population of nanopore-nanodisc complexes comprising the native nanopore protein.

Embodiment 12. The method of embodiment 11, wherein the step of purifying the population of nanopore-nanodisc complexes comprises one or both of size-exclusion chromatography and immobilized metal affinity chromatography.

Embodiment 13. The method of embodiment 11, wherein the aqueous mixture further comprises a detergent, wherein the final concentration of the detergent is from over 14 mM to 40 mM.

Embodiment 14. The method of embodiment 13, wherein the first lipid is 1,2-diphytanoyl-sn-glycero-3-phosphocholine (DPhPC), the MSP is MSP1D1, or a variant thereof, the nanopore protein is α-hemolysin (α-HL) or a variant thereof, the detergent is cholate, and the second lipid is 1,2-diphytanoyl-sn-glycero-3-phosphoethanolamine (DPhPE).

Embodiment 15. The method of embodiment 14, wherein the molar ratio of lipid to MSP to nanopore protein is about 101:6:1 or about 120:6:1.

Embodiment 16. A composition comprising a nanopore-nanodisc complex in an aqueous buffer, wherein the nanopore-nanodisc complex comprises a native nanopore protein, a membrane scaffold protein (MSP), and a lipid and wherein the aqueous buffer comprises a detergent.

Embodiment 17. The composition of embodiment 16, wherein the native nanopore protein is α-hemolysin (α-HL) or a variant thereof, the MSP is MSP1D1, or a variant thereof, the lipid is 1,2-diphytanoyl-sn-glycero-3-phosphocholine (DPhPC), and the detergent is cholate.

Embodiment 18. The composition of embodiment 17, wherein the molar ratio of lipid to MSP to nanopore protein is about 101:6:1 or about 120:6:1 and the concentration of cholate is from over 14 mM to 40 mM.

Embodiment 19. A composition comprising a lyophilized powder comprising a nanopore-nanodisc complex, wherein the nanopore-nanodisc complex comprises a native nanopore protein, a membrane scaffold protein (MSP), and a lipid.

Embodiment 20. The composition of embodiment 19, wherein the native nanopore protein is α-hemolysin (α-HL) or a variant thereof, the MSP is MSP1D1, or a variant thereof, and the lipid is 1,2-diphytanoyl-sn-glycero-3-phosphocholine (DPhPC).

Embodiment 21. The composition of embodiment 20, wherein the molar ratio of lipid to MSP to nanopore protein is about 101:6:1 or about 120:6:1.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Furthermore, the written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

Other nonlimiting embodiments are within the following claims. The patent may not be interpreted to be limited to the specific examples or nonlimiting embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A method of making a detection apparatus comprising one or more native nanopore proteins, comprising the steps of:

(a) forming an aqueous mixture comprising a nanopore protein, a membrane scaffold protein (MSP), and a first lipid to produce a sample of nanodisc-nanopore protein complexes, wherein a population of the nanodisc-nanopore protein complexes in the sample each comprise a native nanopore protein;

(b) providing a solid support comprising one or more apertures, wherein a membrane is formed over each of the apertures, wherein the membrane comprises a second lipid, and wherein the membrane separates a cis chamber from a trans chamber in the detection apparatus; and (c) contacting the one or more membranes with the population of nanopore-nanodisc complexes comprising the native nanopore protein to assimilate a native nanopore protein into each of the membranes;

wherein the aqueous mixture further comprises a detergent, wherein the final concentration of the detergent is from about 14 mM to about 40 mM;

wherein the first lipid is 1.2-diphytanoyl-sn-glycero-3-phosphocholine (DPhPC), the MSP is MSP1D1, or a variant thereof, the nanopore protein is α-hemolysin (α-HL) or a variant thereof, the detergent is cholate, and the second lipid is 1,2-diphytanoyl-sn-glycero-3-phosphoethanolamine (DPhPE); and wherein the molar ratio of first lipid to MSP to nanopore protein is about 101:6:1 or about 120:6:1.

2. The method of claim 1, further comprising the step of purifying the population of nanopore-nanodisc complexes comprising the native nanopore protein from the aqueous mixture prior to the step of contacting the one or more membranes with the population of nanopore-nanodisc complexes comprising the native nanopore protein.

3. The method of claim 2, wherein the step of purifying the population of nanopore-nanodisc complexes comprising the native nanopore protein comprises one or both of size-exclusion chromatography and affinity chromatography.

4. The method of claim 1, wherein the solid support comprises a plurality of apertures, wherein a membrane is formed over each of the plurality of apertures, and wherein each of the membranes is contacted with the nanopore-nanodisc complex comprising the native nanopore protein.

* * * * *